United States Patent
Sharifi-Mehr

(10) Patent No.: US 8,753,399 B2
(45) Date of Patent: Jun. 17, 2014

(54) DYNAMIC INTERBODY DEVICE

(75) Inventor: Amir Ali Sharifi-Mehr, Bloomingdale, NJ (US)

(73) Assignee: Stryker Spine (FR)

( * ) Notice: Subject to any disclaimer, the term of this patent is extended or adjusted under 35 U.S.C. 154(b) by 1034 days.

(21) Appl. No.: 11/601,596

(22) Filed: Nov. 17, 2006

(65) Prior Publication Data

US 2007/0123990 A1 May 31, 2007

Related U.S. Application Data

(60) Provisional application No. 60/740,095, filed on Nov. 28, 2005.

(51) Int. Cl.
A61F 2/44 (2006.01)

(52) U.S. Cl.
USPC .............. 623/17.15; 623/17.13; 623/17.16

(58) Field of Classification Search
USPC .............. 623/17.11–17.16; 100/202; 108/66; 16/287; 220/837, 847
See application file for complete search history.

(56) References Cited

U.S. PATENT DOCUMENTS

| | | | |
|---|---|---|---|
| 4,997,432 A | | 3/1991 | Keller |
| 5,299,980 A | * | 4/1994 | Agius ............................. 464/99 |
| 5,320,644 A | * | 6/1994 | Baumgartner ............. 623/17.16 |
| 5,534,029 A | | 7/1996 | Shima |
| 5,556,431 A | | 9/1996 | Buttner-Janz et al. |
| 5,562,738 A | | 10/1996 | Boyd et al. |
| 5,676,702 A | * | 10/1997 | Ratron ......................... 623/17.16 |
| 5,782,832 A | * | 7/1998 | Larsen et al. ............... 623/17.11 |
| 6,001,130 A | | 12/1999 | Bryan et al. |
| 6,080,158 A | * | 6/2000 | Lin ................................. 606/247 |
| 6,113,637 A | | 9/2000 | Gill et al. |
| 6,136,031 A | * | 10/2000 | Middleton ................. 623/17.16 |
| 6,203,437 B1 | * | 3/2001 | Durie et al. ...................... 464/78 |
| 6,395,035 B2 | * | 5/2002 | Bresina et al. .............. 623/17.15 |
| 6,402,785 B1 | * | 6/2002 | Zdeblick et al. ........... 623/17.16 |
| 6,440,169 B1 | * | 8/2002 | Elberg et al. ............... 623/17.16 |
| 6,579,321 B1 | * | 6/2003 | Gordon et al. ............. 623/17.16 |
| 6,582,468 B1 | * | 6/2003 | Gauchet ..................... 623/17.16 |
| 6,964,686 B2 | * | 11/2005 | Gordon ...................... 623/17.14 |
| 7,166,131 B2 | * | 1/2007 | Studer et al. ............... 623/17.16 |
| 7,331,994 B2 | * | 2/2008 | Gordon et al. ............. 623/17.13 |
| 2006/0247781 A1 | * | 11/2006 | Francis ....................... 623/17.16 |
| 2008/0004704 A1 | * | 1/2008 | Katz ........................... 623/17.16 |

FOREIGN PATENT DOCUMENTS

| | | | | |
|---|---|---|---|---|
| DE | 35 297 61 | | 7/1986 | |
| WO | WO 2004/054479 | * | 7/2004 | ............... A61F 2/44 |
| WO | WO 2004/054479 A1 | * | 7/2004 | ............... A61F 2/44 |

* cited by examiner

*Primary Examiner* — Michael T Schaper
(74) *Attorney, Agent, or Firm* — Lerner, David, Littenberg, Krumholz & Mentlik, LLP

(57) ABSTRACT

An intervertebral implant includes an upper plate having an outer surface and an inner surface, a lower plate having an outer surface and an inner surface, and an intermediate plate having a first surface opposing the inner surface of the upper plate and a second surface opposing the inner surface of the lower plate. The implant includes a first flexible hinge that couples the upper plate and the intermediate plate, and a second flexible hinge that couples the intermediate plate and the lower plate, the first flexible hinge extending along a first axis and the second flexible hinge extending along a second axis that traverses the first axis.

23 Claims, 14 Drawing Sheets

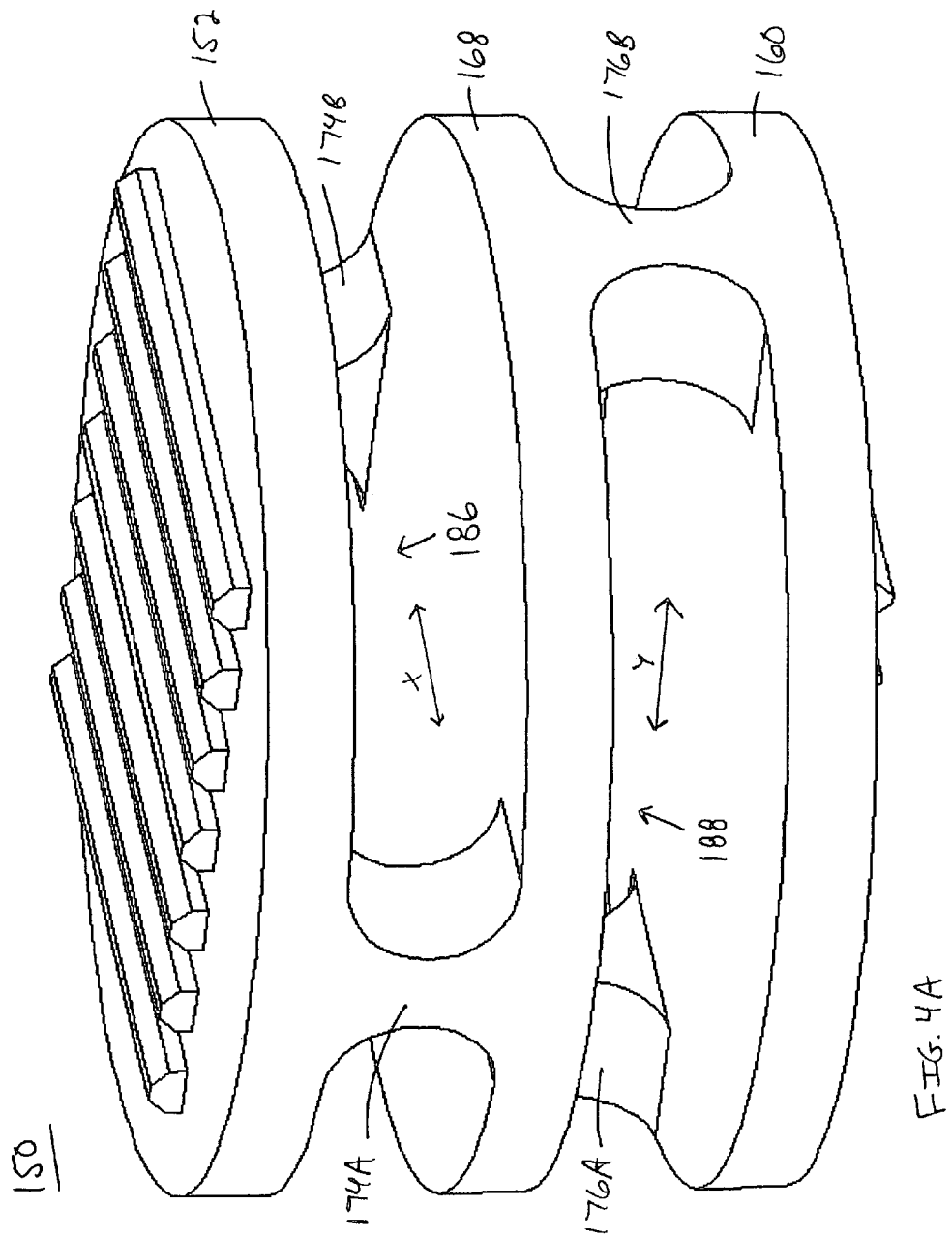

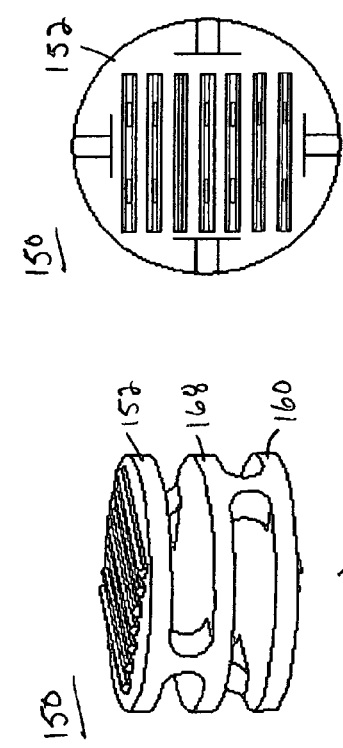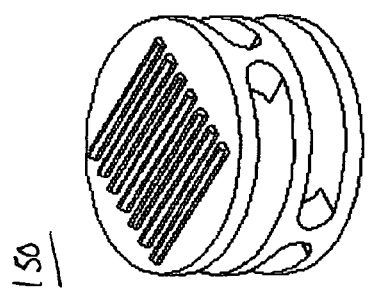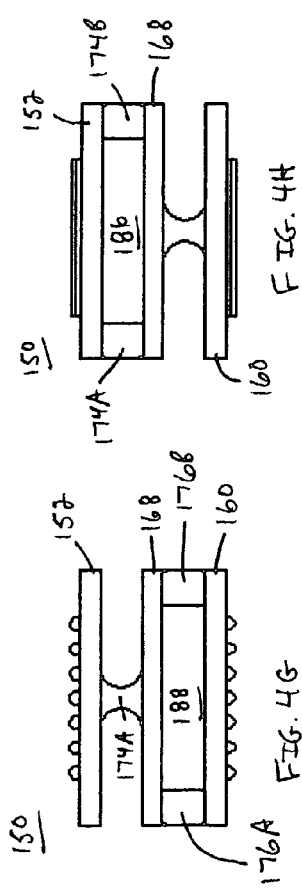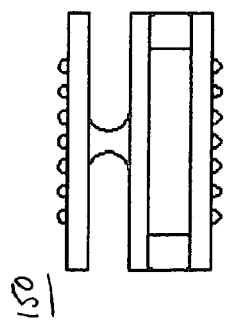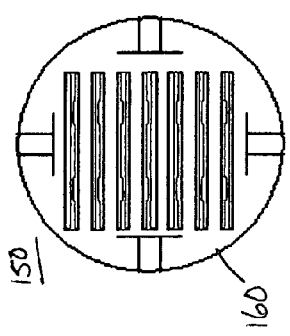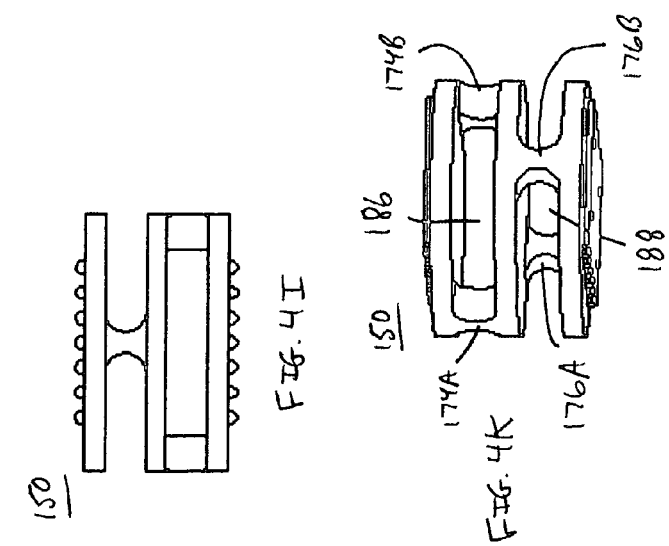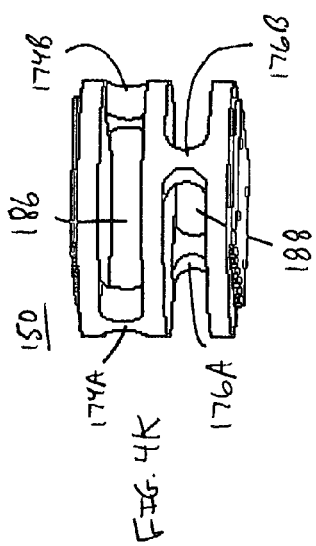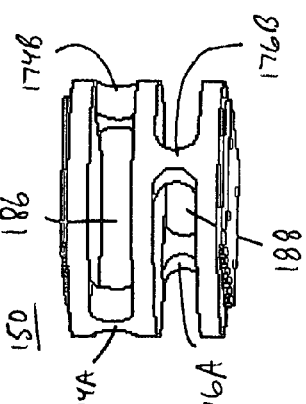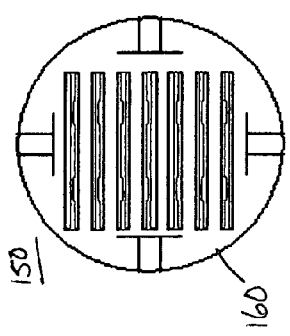

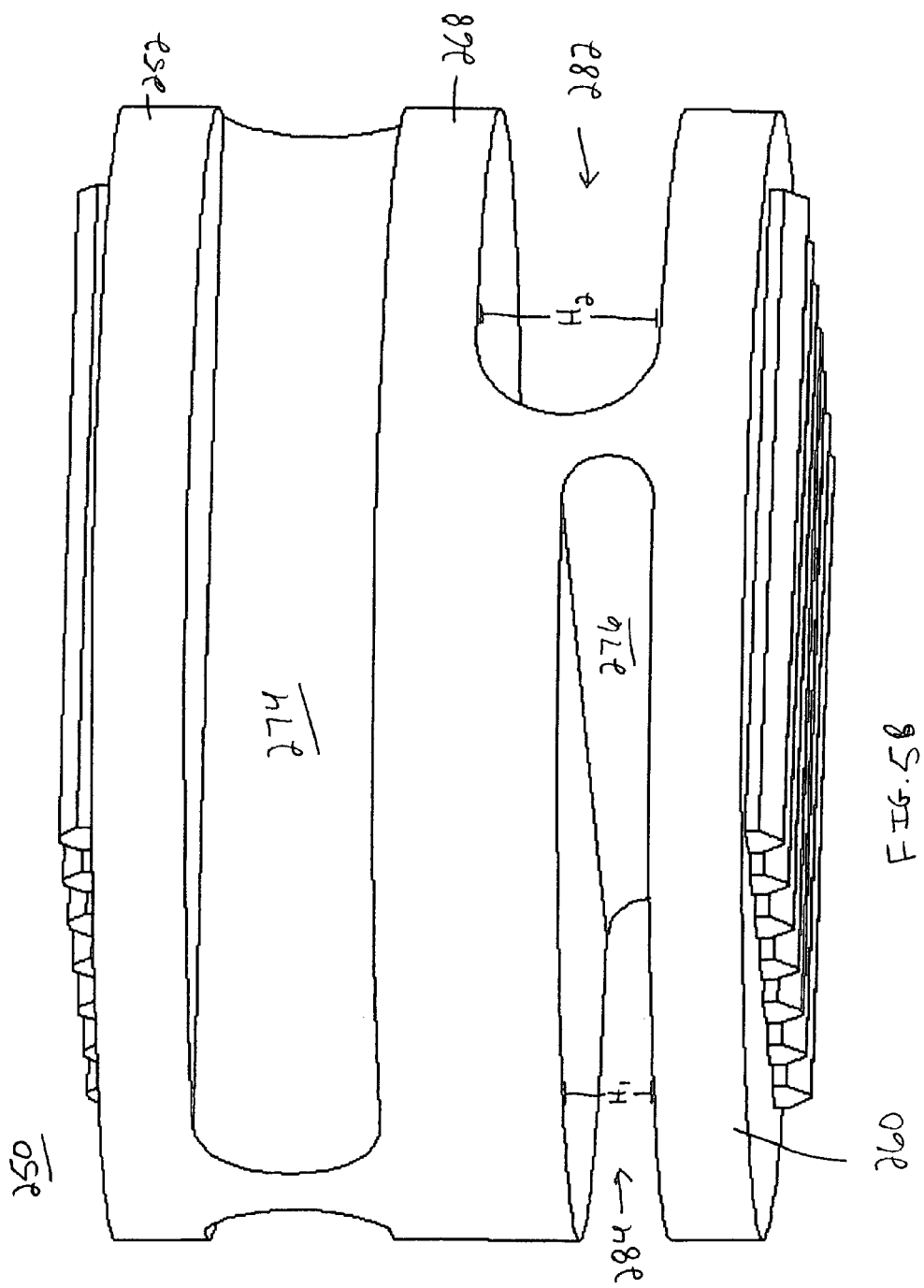

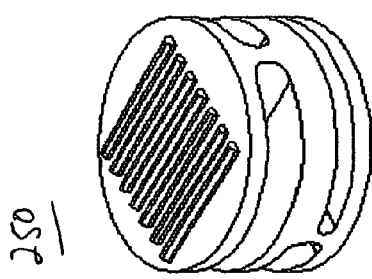
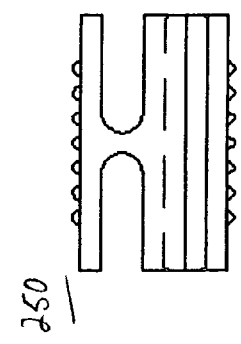
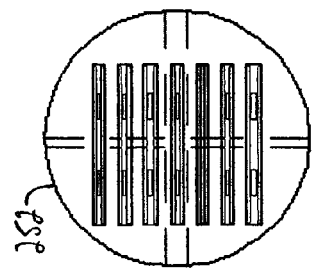
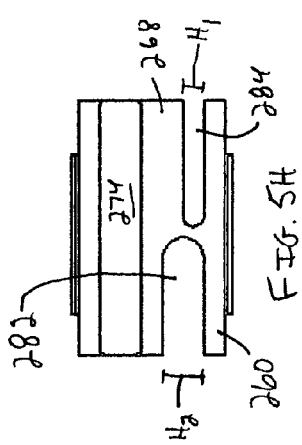
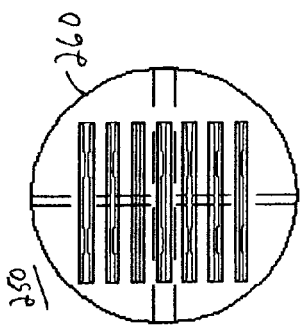
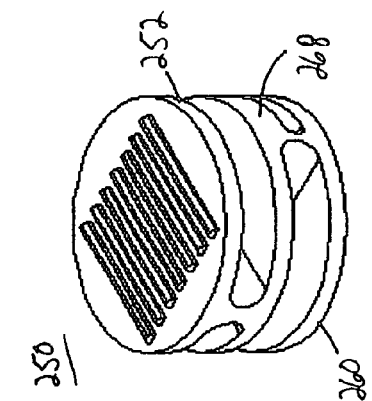
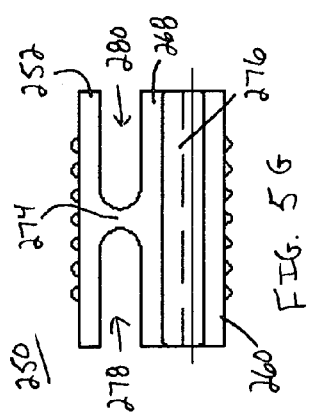

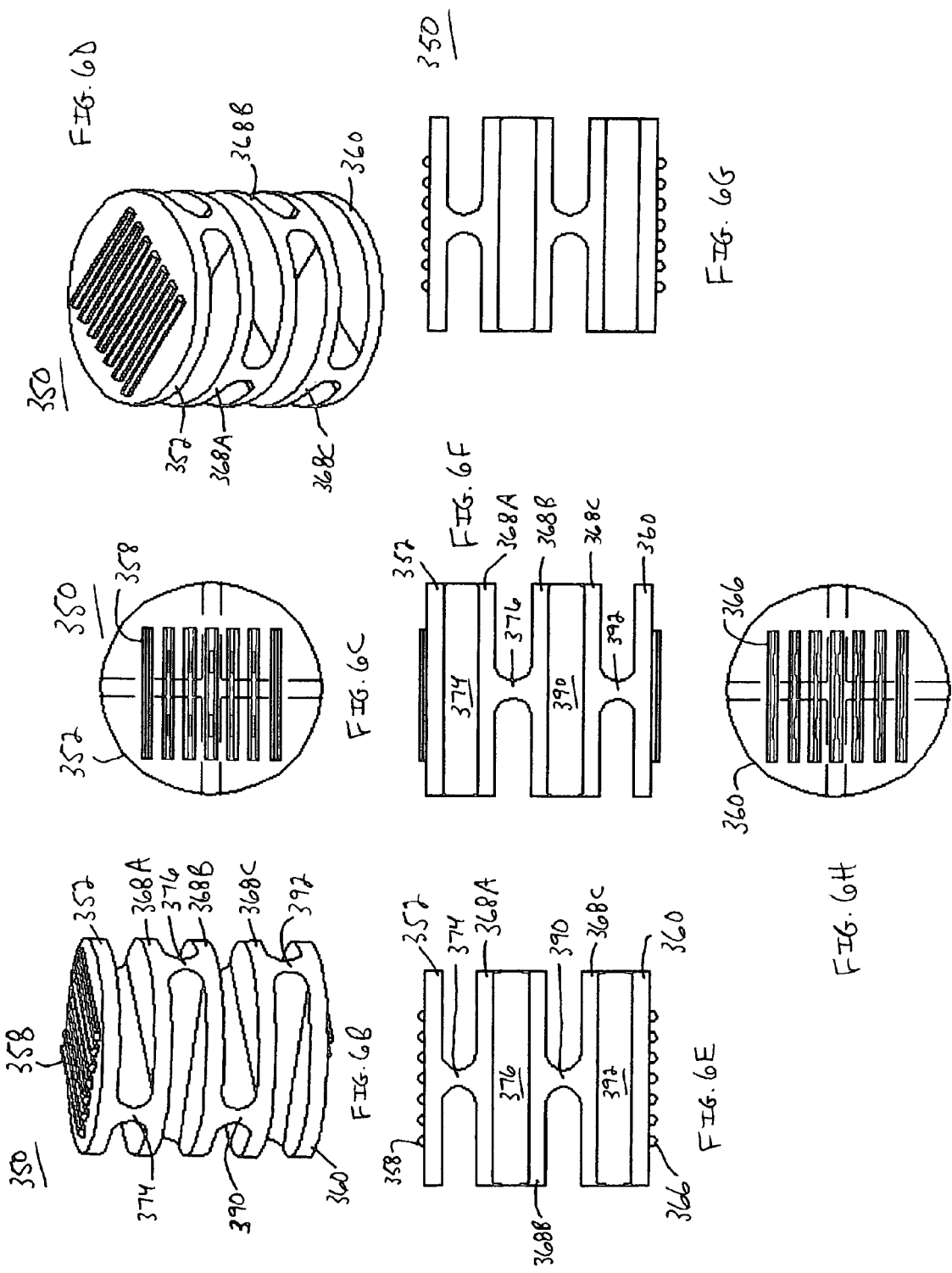

DYNAMIC INTERBODY DEVICE

CROSS-REFERENCE TO RELATED APPLICATIONS

The present application claims benefit of U.S. Provisional Application Ser. No. 60/740,095, filed Nov. 28, 2005, the disclosure of which is hereby incorporated by reference herein.

BACKGROUND OF THE INVENTION

The present invention is related to orthopedic implants and is more particularly related to intervertebral implants.

The human spinal column has more than twenty discrete bones sequentially coupled to one another by a tri-joint complex that consists of an anterior disc and two posterior facet joints, the anterior discs of adjacent bones being cushioned by cartilage spacers referred to as intervertebral discs. The more than twenty bones are anatomically categorized in one of four classifications: cervical, thoracic, lumbar, or sacral. The cervical portion of the spine extends from the base of the skull and includes the first seven vertebrae. The intermediate twelve vertebrae make up the thoracic portion of the spine. The lower portion of the spine comprises five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in dose proximity. In spite of these complications, the spine is a highly flexible structure, capable of a high degree of curvature and twist in nearly every direction.

The intervertebral disc disposed between the vertebrae in the human spine has a peripheral fibrous shroud (the annulus) that surrounds a spheroid of flexibly deformable material (the nucleus). The nucleus comprises a hydrophilic, elastomeric cartilaginous substance that cushions and supports the separation between the bones. The nucleus also permits articulation of adjacent vertebral bones relative to one another to the extent such articulation is allowed by the other soft tissue and bony structures surrounding the disc. The additional bony structures that define pathways of motion in various modes include the posterior joints (the facets) and the lateral intervertebral joints (the unco-vertebral joints). Soft tissue components, such as ligaments and tendons, constrain the overall segmental motion as well.

Traumatic, genetic, and long term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

While spine arthroplasty has been developing in theory over the past several decades, and has even seen a number of early attempts in the lumbar spine show promising results, it is only recently that arthoplasty of the spine has become a truly realizable promise. The field of spine arthroplasty has several classes of devices. The most popular among these are: (a) the nucleus replacements, which are characterized by a flexible container filled with an elastomeric material that can mimic the healthy nucleus; and (b) the total disc replacements, which are designed with rigid endplates which house a mechanical articulating structure that attempts to mimic and promote the healthy segmental motion.

Among these solutions, the total disc replacements have begun to be regarded as the most probable long-term treatments for patients having moderate to severe lumbar disc degeneration. In the cervical spine, it is likely that these mechanical solutions will also become the treatment of choice. At present, there are at least two devices being tested clinically in humans for the indication of cervical disc degeneration. The first of these is the Bryan disc, disclosed in part in U.S. Pat. No. 6,001,130. The Bryan disc is comprised of a resilient nucleus body disposed in between concaval-covex upper and lower elements that retain the nucleus between adjacent vertebral bodies in the spine. The concaval-convex elements are L-shaped supports that have anterior wings that accept bones screws for securing to the adjacent vertebral bodies.

The second of these devices being clinically tested is the Bristol disc, disclosed substantially in U.S. Pat. No. 6,113,637. The Bristol disc is comprised of two L-shaped elements, with corresponding ones of the legs of each element being interposed between the vertebrae and in opposition to one another. The other of the two legs are disposed outside of the intervertebral space and include screw holes through which the elements may be secured to the corresponding vertebra; the superior element being secured to the upper vertebral body and the inferior element being attached to the lower vertebral body. The opposing portions of each of the elements comprise the articulating surfaces that include an elliptical channel formed in the lower element and a convex hemispherical structure disposed in the channel.

Further improvements include U.S. Pat. No. 5,534,029 to Shima, which discloses an articulated vertebral body spacer including a pair of upper and lower joint pieces inserted between opposing vertebrae. The lower joint piece includes a convex portion formed on a central portion of its upper surface and having a convex sliding contact surface, and a stopper surface surrounding the convex portion. The upper joint piece includes a concave portion formed on a central portion of its lower surface and having a concave sliding contact surface which is in sliding contact with the convex sliding contact surface, and an abutment surface that surrounds the concave portion and abuts against the stopper surface. A cavity for allowing the upper joint piece to pivot in response to movement of the opposing vertebral bodies is formed between the abutment surface and the stopper surface.

DE 3529761 discloses a prosthesis for an intervertebral disc including two plates 1 with a spacer disc 4 therebetween. The two plates 1 each have a concave center and a flat annular rim 2 with spikes 3. The disc spacer 4 has a convex center and a flat rim with an annular groove 6. The prosthesis is used for spanning the gap between opposing vertebral faces remaining firmly in place while permitting natural movement of the spine.

U.S. Pat. No. 4,997,432 to Keller discloses a prosthesis including two stop plates 3 and a sliding body 4 arranged therebetween. The outer surfaces of the stop plates 3 have an essentially planar surface 5 provided with tooth-like projection 6 that penetrate into the vertebral bodies to fix the stop plates 3 securely to the vertebral bodies 1. The opposite side surfaces of the stop plates 3 include essentially spherical-shell-shaped recesses 7. The sliding core 4 has a spherical-shell-shaped projections 8 corresponding to the spherical-shell-shaped recesses 7. The stop plates 3 are made of metal and the sliding body 4 is made of a synthetic material.

U.S. Pat. No. 5,562,738 to Boyd et al. discloses an implant device having an ellipsoidally-shaped ball and socket oriented so that their greatest lengths are disposed along a first axis transverse to the anterior and posterior ends and their shortest lengths are disposed along a second axis which is perpendicular to the first axis along surface. A first joint surface is sloped away from the socket while a second joint surface remains flat. The degree of slope determines the amount of relative rotation between joint surfaces, and the first joint surface is sloped to provide for up to 5° of lateral bending in either direction, up to 5° of extension and up to 5° of Flexion.

Finally, U.S. Pat. No. 5,556,431 to Buttner-Janz discloses an intervertebral disc endoprosthesis that is inserted between two vertebrae and has a bottom plate and a top plate that are connected to vertebral endplates. Referring to FIG. 1, the device includes prosthesis plates 1 and 2 and prosthesis core 3 cooperated via spherical surfaces 4. The core 3 has an edge rim 5 that limits its range of movement and insures, even under extreme conditions cohesion of the prosthesis. The endplate 6 of the prosthesis plates 1, 2 lie on the end surfaces of the vertebrae and are provided with teeth 7, which, under load, penetrate into the vertebrae and thus secure the prosthesis in situ. Bore holes 8 are arranged symmetrically on both side of the central plane, running from ventral to dorsal, of the vertebrae and in the area of the front edge of the prosthesis plates 1, 2 to receive bone screws 9.

In spite of the above-noted advances in the art, there remains a need for an improved vertebral body spacer having enhanced stabilization and bone fusion characteristics.

With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, a prior art intervertebral body cage 30 includes a tubular metal body 32 having threads 34 on an external surface thereof. Each cage 30 is inserted transverse to the axis of the spine 36, into preformed cylindrical holes at the junction of adjacent vertebral bodies (in FIG. 2 the pair of cages 30 are inserted between the fifth lumbar vertebra (L5) and the top of the sacrum (S1)). The two cages 30 are generally inserted side by side with the external threading 34 tapping into the lower surface of the vertebral bone above (L5), and the upper surface of the vertebral bone (S1) below. The cages 30 include holes 38 through which the adjacent bones are to grow. Additional materials, for example autogenous bone graft materials, may be inserted into the hollow interior 40 of the cage 30 to incite or accelerate the growth of the bone into the cage. End caps (not shown) are often utilized to hold the bone graft material within the cage. 1.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

Thus, there remains a need for an intervertebral spacer that stabilizes the spine, which enables adjacent vertebrae to move relative to one another, that supports compressive loads and that permits normal motion and rotation of the spinal segments.

SUMMARY OF THE INVENTION

In certain preferred embodiments of the present invention, an intervertebral implant includes an upper plate having an outer surface and an inner surface, the outer surface of the upper plate including one or more bone-engaging projections, and a lower plate having an outer surface and an inner surface, the outer surface including bone-engaging projections. The implant also desirably includes an intermediate plate having a first surface that faces toward the inner surface of the upper plate and a second surface that faces toward the inner surface of the lower plate.

The implant also desirably includes a first flexible hinge that extends between the upper plate and the intermediate plate, and a second flexible hinge that extends between the intermediate plate and the lower plate, the first flexible hinge extending along a first axis and the second flexible hinge extending along a second axis that traverses the first axis. The implant may also have first and second slots that extend between the upper plate and the intermediate plate, on opposite sides of the first flexible hinge, the slots preferably having a height that extends between the inner surface of the upper plate and the first surface of the intermediate plate. The implant may also have third and fourth slots formed on opposite sides of the second flexible hinge, the slots preferably having a height that extends between the inner surface of the lower plate and the second surface of the intermediate plate. The first and second slots preferably allow the upper plate and the intermediate plate to angulate relative to one another about the first axis, and the third and fourth slots enable the intermediate plate and the lower plate to angulate relative to one another about the second axis for enabling flexion/extension about one of the first and second axes and lateral bending about the other of the first and second axes.

In other preferred embodiments, one or more of the flexible hinges may have a space formed therein or at least partially extending therethrough for enhancing the flexibility of one of more levels of the implant. In yet further preferred embodiments of the present invention, one or more of the slots formed between the plates may have a height that is different than one or more of the other slots between the plates for promoting more flexibility in one direction and relatively less flexibility in another direction. In still other preferred embodiments of the present invention, the implant may have two or more intermediate plates between the upper and lower plates, with each of the plates being interconnected by a flexible hinge.

In another preferred embodiment of the present invention, an intervertebral implant includes an upper plate having an outer surface and an inner surface, and a lower plate coupled with the upper plate, the lower plate having an outer surface and an inner surface. The implant includes first, second and third intermediate plates disposed between the inner surfaces of the upper plate and the lower plate. The first intermediate plate is connected with the upper plate by a first flexible hinge and the third intermediate plate is connected with the lower plate by a second flexible hinge. The second intermediate plate is disposed being the first and third intermediate plates. The second intermediate plate is connected with the first intermediate plate by a first intermediate hinge and is connected with the third intermediate plate by a second intermediate hinge. The first flexible hinge and the second intermediate hinge extend along axes that lie in a first plane and the second flexible hinge and the second intermediate hinge extend along axes that lie in a second plane that intersects the first plane.

In another preferred embodiment of the present invention, an intervertebral implant includes an upper plate having an outer surface and an inner surface, the outer surface of the upper plate including one or more bone-engaging projections, and a lower plate having an outer surface and an inner surface, the outer surface of the lower plate including bone-engaging projections. The implant preferably includes an intermediate plate having a first surface that faces toward the inner surface of the upper plate and a second surface that faces toward the inner surface of the lower plate. The implant desirably includes a first flexible hinge extending between the upper plate and the intermediate plate, and a second flexible hinge extending between the intermediate plate and the lower plate, the first flexible hinge extending along a first axis and the second flexible hinge extending along a second axis that traverses the first axis. The implant preferably includes first and second slots that extend between the upper plate and the intermediate plate, on opposite sides of the first flexible hinge, the slots preferably having a height that extends between the inner surface of the upper plate and the first surface of the intermediate plate. The implant also desirably includes third and fourth slots formed on opposite sides of the second flexible hinge, whereby the first and second slots allow the upper plate and the intermediate plate to angulate relative to one another about the first axis, and the third and fourth slots enable the intermediate plate and the lower plate to angulate relative to one another about the second axis. The implant is adapted for flexion and extension about one of the first and second axes and lateral bending about the other of the first and second axes.

In highly preferred embodiments, the implant is formed of a single piece of material, such as a biocompatible material, whereby all of the parts are integrally formed together.

These and other preferred embodiments of the present invention will be described in more detail below.

BRIEF DESCRIPTION OF THE DRAWINGS

FIGS. 3A-3I show a dynamic intervertebral implant, in accordance with certain preferred embodiments of the present invention.

FIGS. 4A-4K show a dynamic intervertebral implant, in accordance with other preferred embodiments of the present invention.

FIGS. 5A-5J show a dynamic intervertebral implant, in accordance with another preferred embodiment of the present invention.

FIGS. 6A-6H show a dynamic intervertebral implant, in accordance with still other preferred embodiments of the present invention.

DETAILED DESCRIPTION

Figure 1:
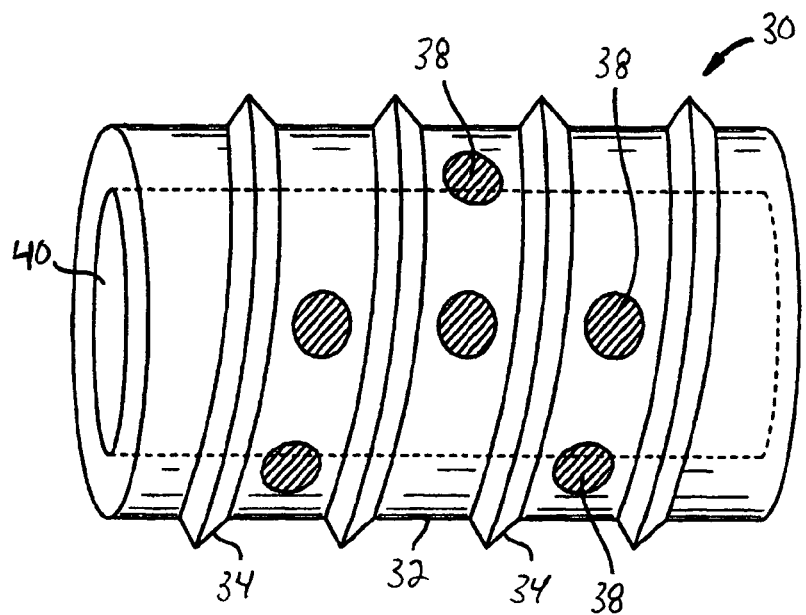
FIG. 1 shows a prior art vertebral implant.
Figure 2:
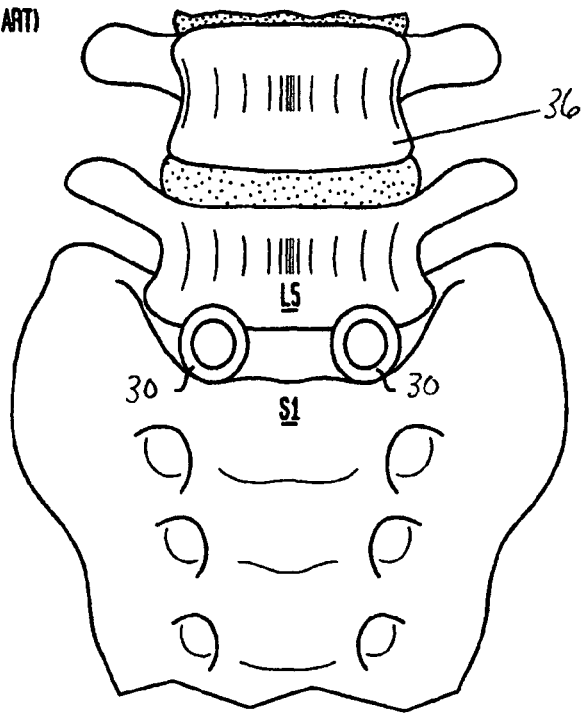
FIG. 2 shows prior art implant of FIG. 1 after being inserted into a disc space of a spine.

FIGS. 3A-3I show a dynamic interbody implant 50, in accordance with certain preferred embodiments of the present invention. The implant 50 includes an upper plate 52 having an outer surface 54 and an inner surface 56. The outer surface 54 of the upper plate 52 includes one or more bone-engaging projections 58 such as teeth, ridges or spikes. The implant 50 also includes a lower plate 60 having an outer surface 62 and an inner surface 64. The outer surface 62 includes bone-engaging projections 66 such as spikes, ridges, or teeth. The use of the terminology upper and lower plates is not meant to limit the scope of the invention or the orientation of the implant when it is inserted into a body. For example, the implant can be inserted with the lower plate over the upper plate. Implant 50 also includes an intermediate plate 68 having a first surface 70 that faces toward the inner surface 56 of upper plate 52 and a second surface 72 that faces toward the inner surface 64 of lower plate 60.

Implant 50 also preferably includes a first flexible hinge 74 that extends between the upper plate 52 and the intermediate plate 68, and a second flexible hinge 76 that extends between the intermediate plate 68 and the lower plate 60. The first flexible hinge 74 preferably extends along an axis X and the second flexible hinge 76 preferably extends along an axis Y that traverses axis X. In certain preferred embodiments, the axes X, Y are angled relative to one another. In other preferred embodiments, the axes X, Y are substantially perpendicular to one another. As will be described in more detail below, the axis of the hinges may be substantially perpendicular to one another so that the implant allows for flexion/extension along one of the axes and lateral bending along the other of the axes.

Implant 50 preferably includes first and second slots 78, 80 that extend between the upper plate 52 and the intermediate plate 68. The first and second slots 78, 80 are preferably formed on opposite sides of first flexible hinge 74. The slots 78, 80 preferably have a height that extends between the inner surface 56 of upper plate 52 and the first surface 70 of intermediate plate 68. The height of the slots may be modified depending upon the amount of flexibility that is desired between upper plate 52 and intermediate plate 68.

Implant 50 also preferably includes third and fourth slots 82, 84 formed on opposite sides of the second flexible hinge 76. The first and second slots 78, 80 preferably allow upper plate 52 and intermediate plate 68 to angulate relative to one another about axis X. The third and fourth slots 82, 84 preferably enable intermediate plate 68 and lower plate 60 to angulate relative to one another about axis Y. Thus, the implant 50 shown in FIGS. 3A-3I enables flexion and extension about one axis of the implant and lateral bending about another axis of the implant.

Each of the flexible hinges 74, 76 preferably has a width. The width of the respective flexible hinges may be modified to provide for more or less flexibility and/or more or less angulation between the plates 52, 60 and 68.

In certain preferred embodiments, the implant 50 may be formed from a solid block of material, such as a biocompatible material. The block of material may be titanium, a thermoplastic material such as peek, stainless steel, nitinol or commercially pure titanium. The block of material may be milled or machined to form the slots on both sides of the flexible hinges. The outer faces of the upper and lower plates may also be milled to form the bone engaging projections thereon.

Although the present invention is not limited by any particular theory of operation, it is believed that the implant disclosed herein provides an improved alternative to fusion for degenerative disk disease. The implant is preferably a one-piece device, which provides a number of improvements over the multi-piece designs known from the prior art. As is well known to those skilled in the art, multi-part devices may be difficult to implant due to problems associated with attempting to maintain the two or more parts of the implant together and in a certain orientation during implantation. Moreover, a multi-part implant may become disassembled after implantation.

In certain preferred embodiments, the implant may be used to replace a segment of the spine that has been removed such as a disc, multiple discs, or one or more discs and one or more vertebrae. Thus, it is contemplated that the present invention can span a spinal segment that has had two or more vertebral bodies removed. The implant of the present invention uses flexible hinges or mechanical flexures, which provide support to the spinal column while maintaining motion at the corrected spinal segment. By allowing motion in the corrected segment, less stress is applied to adjacent spinal segments.

In certain preferred embodiments, the implant disclosed herein functions similarly to a spring and is designed to be axially rigid to support loads on the spine, while allowing compliance about the flexible hinges. The spring constant of the flexible hinges may be adjusted by changing the width of the flexible hinges and/or by changing the height of the slots extending between the plates. Thus, the flexibility of the implant may be modified by thickening or thinning the flexible hinges, or by removing material from the center of the flexible hinges. Moreover, depending upon the specific location of the spine that will receive the implant, the height of the implant may be adjusted to span various heights. The height of the slots between the plates may also be modified to control the amount of angulation that may occur between adjacent plates. Controlling the slot height may also protect the flexible hinges from becoming over-stressed. The single-piece design will also facilitate implantation of the device because the surgeon does not have to worry about holding two or more pieces together at certain orientations. Thus, the surgeon only has to grasp a one-piece device and does not have to be concerned about the particular orientation of multiple parts relative to one another during the implantation procedure.

FIGS. 4A-4K show a spinal implant 150, in accordance with other preferred embodiments of the present invention. The spinal implant includes an upper plate 152, a lower plate 160, and an intermediate plate 168 provided between the upper and lower plates. The upper and intermediate plates 152, 168 are interconnected by first flexible hinges 174A, 174B. The lower plate 160 and the intermediate plate 168 are interconnected by second flexible hinges 176A, 176B. The first flexible hinges 174A, 174B preferably enable the upper plate 152 and the intermediate plate 168 to angulate relative to one another about an axis X. The second flexible hinges 176A, 176B preferably enable the lower plate 160 and the intermediate plate 168 to angulate relative to one another about an axis Y. The axes X, Y are preferably angled to one another and in highly preferred embodiments are substantially perpendicular to one another. As a result, after being implanted in a spinal segment, the implant 150 allows flexion/extension and lateral bending of the spinal segment.

The implant 150 shown in FIGS. 4A-4K is substantially similar to the implant shown in FIGS. 3A-3I described above. However, the implant shown in FIGS. 4A-4K includes a first space 186 extending between first hinges 174A, 174B and a second space 188 second hinges 176A, 176B. Forming the spaces 186, 188 may be accomplished by milling a block of material to form a space extending through one of the flexible hinges shown in FIGS. 3A-3I. Although the present invention is not limited by any particular theory of operation, it is believed that the material removed between the hinges enhances the flexibility of the plates relative to one another. In other preferred embodiments, one of the hinges may be solid as shown in the embodiment of FIGS. 3A-3I and one of the hinges may have a space formed therein as shown in the embodiment of FIGS. 4A-4K.

FIGS. 5A-5J show an implant 250, in accordance with another preferred embodiment of the present invention. The implant 250 includes an upper plate 252, a lower plate 260, and an intermediate plate 268 disposed between the upper plate 250 and the lower plate 260. The upper plate 252 and the intermediate plate 268 are interconnected by a first flexible hinge 274, and the lower plate 260 and the intermediate plate 268 are interconnected by a second flexible hinge 276. The implant includes a first slot 278 and a second slot 280 extending between the upper plate 252 and the intermediate plate 268. The implant also includes a third slot 282 and a fourth slot 284 extending between the lower plate 260 and the intermediate plate 268.

As shown most clearly in FIGS. 5B and 5H, the fourth slot 284 extending between lower plate 260 and intermediate plate 268 has a height $H_1$ that is smaller than the height $H_2$ of third slot 282. As a result, lower plate 260 and intermediate plate 268 are able to have a greater degree of angulation at slot 282 and a lesser degree of angulation at slot 284. This is because the height $H_1$ in slot 284 limits the degree to which intermediate plate 268 and lower plate 260 may angulate relative to one another before the opposing plate surfaces contact one another. In contrast, the greater height $H_2$ of the third slot 284 enables greater angulation between lower plate 260 and intermediate plate 268 before the two plates contact one another. The exact height differential between the third and fourth slots 282, 284 may be modified and/or controlled depending upon the amount of flexibility desired between the plates.

Although the present invention is not limited by any particular theory of operation, it is believed that enabling the plates to angulate to a greater degree in one direction and to a lesser degree in the opposite direction, will provide an implant that more closely matches the physiological performance of the spine. For example, those skilled in the art know that the spine is able to flex to a greater degree than it is able to extend. Thus, the implant of the present invention may be inserted into spinal segment so that it will enable greater flexure of the spinal segment and less extension of the same spinal segment.

In other preferred embodiments, two or more of the slots in an implant may have a different height than the remaining slots of the implant.

In other preferred embodiments, both levels of the implant may have slots on opposite sides of the flexible hinges that have different heights for controlling the amount of angulation between the plates. For example, an implant in accordance with certain preferred embodiments of the present invention may allow flexing to a greater degree than extension and allow lateral bending on one side of the body to a greater degree than lateral bending on the other side of the body.

In still other preferred embodiments of the present invention, a first flexible hinge interconnecting two plates of the implant may have a different thickness than a second flexible hinge interconnecting two plates of the implant.

FIGS. 6A-6H show a dynamic interbody device 350, in accordance with another preferred embodiment of the present invention. The implant 350 includes an upper plate 352 and a lower plate 360. Implant 350 also includes three intermediate plates, namely first intermediate plate 368A, second intermediate plate 368B and third intermediate plate 368C. Implant 350 also has a first flexible hinge 374 interconnecting upper plate 352 and first intermediate plate 368A, a first intermediate hinge 376 interconnecting first intermediate plate 368A and second intermediate plate 368B, and a second intermediate hinge 390 interconnecting second intermediate plate 368B and third intermediate plate 368C. Implant 350 also includes a second flexible hinge 392 interconnecting third intermediate plate 368C and lower plate 360.

Figure 3A:
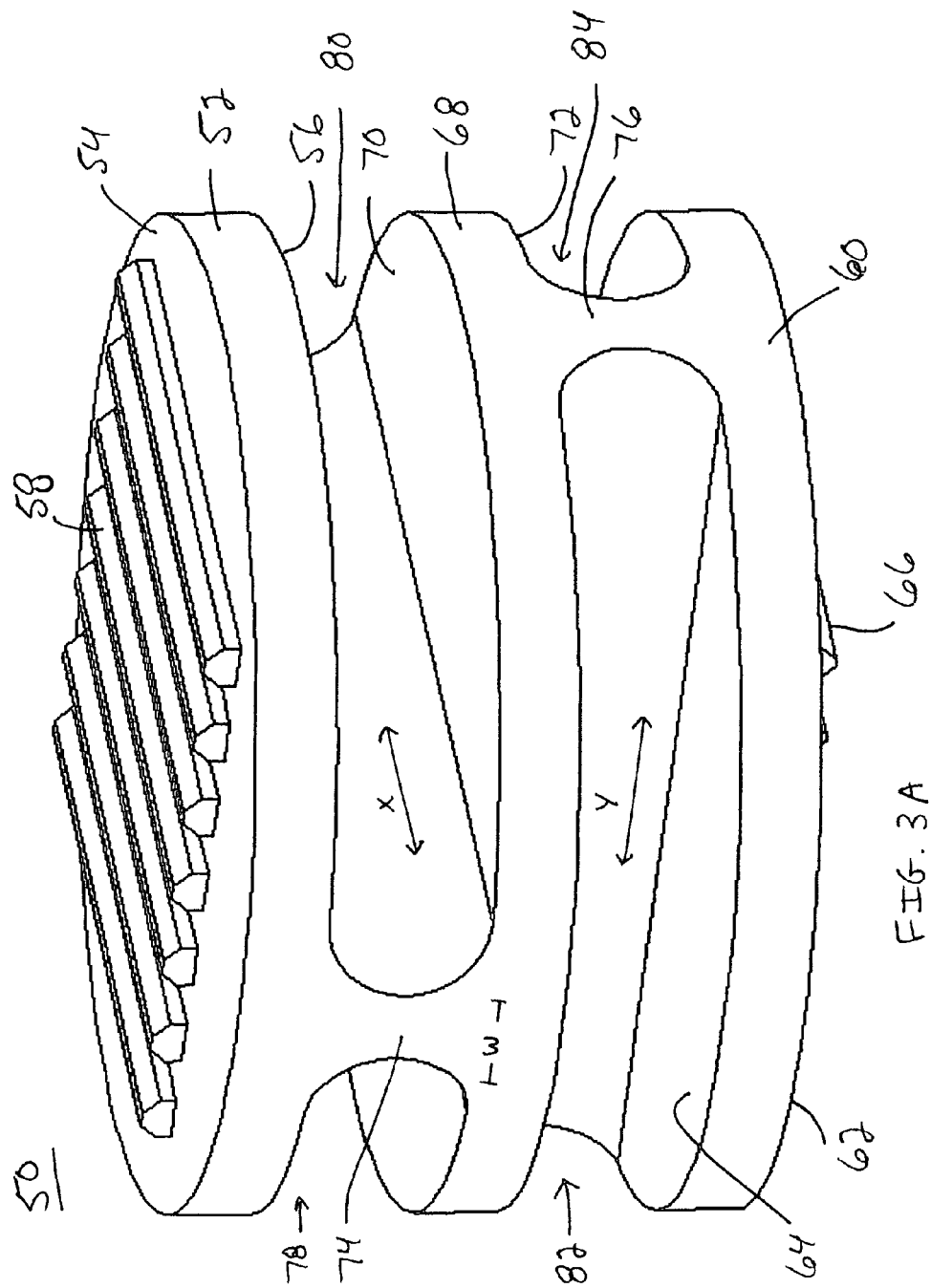
Figure 3B:
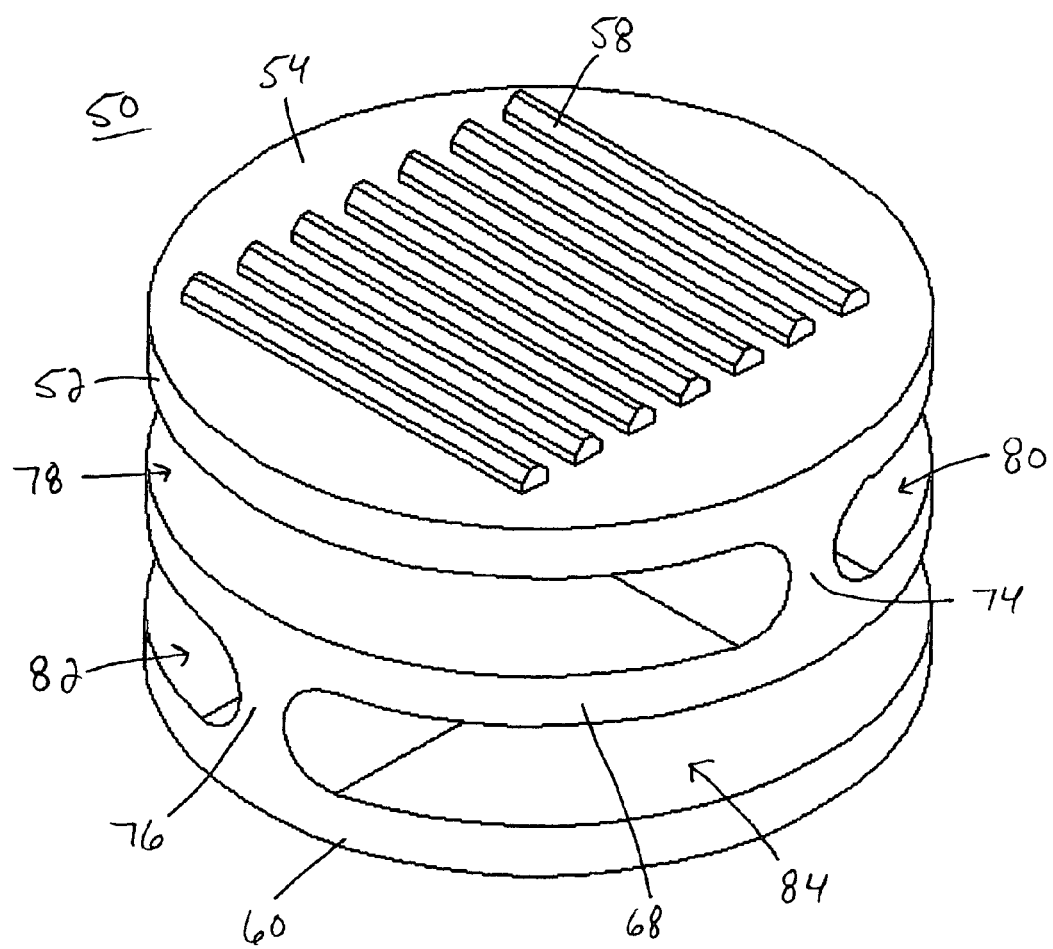
Figure 3C:
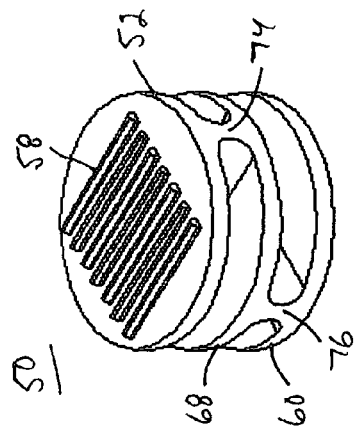
Figure 3H:
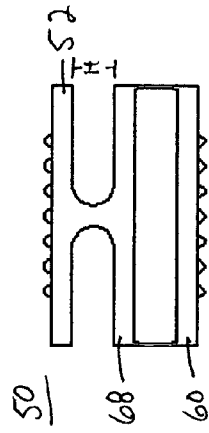
Figure 3D:
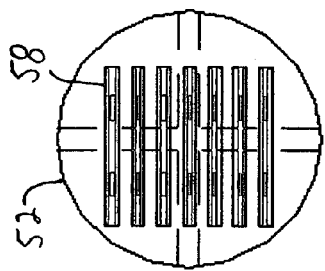
Figure 3G:
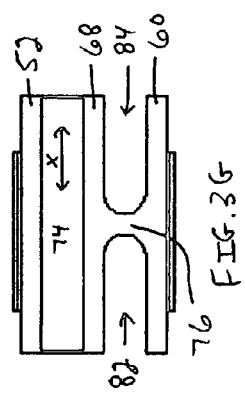
Figure 3I:
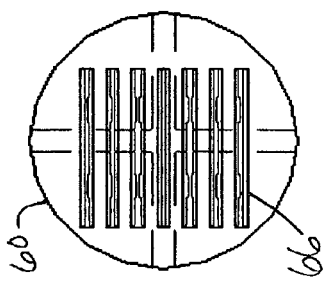
Figure 3C:
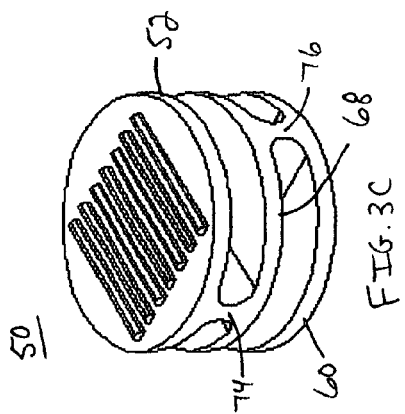
Figure 3F:
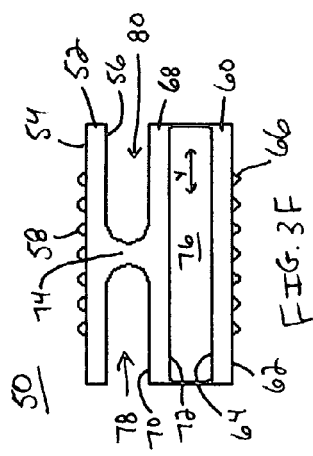
Figure 4B:
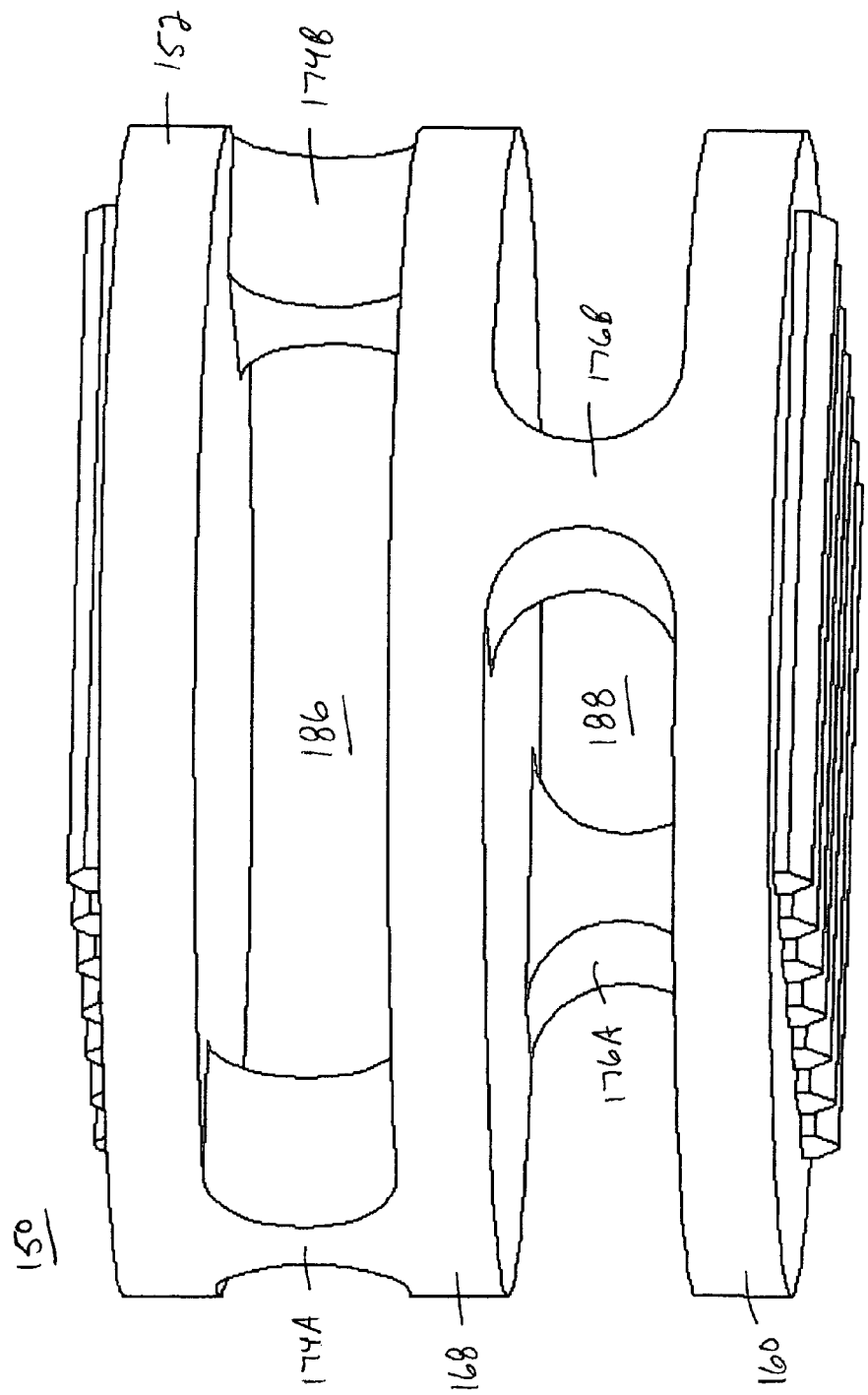
Figure 4C:
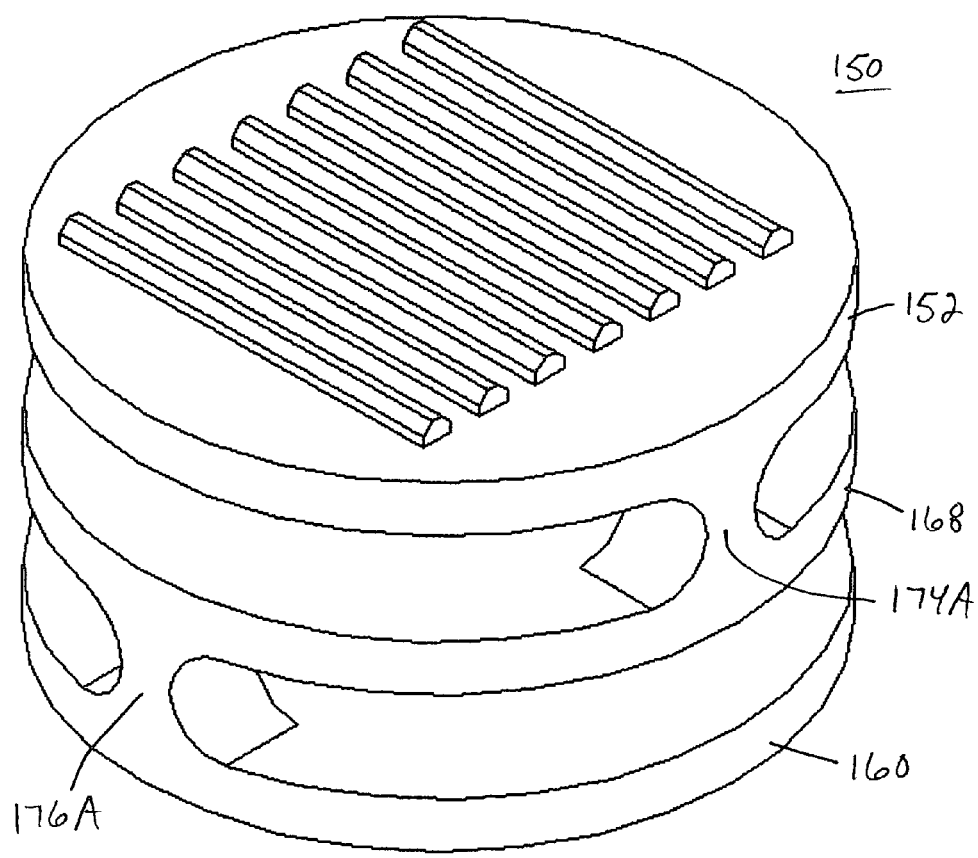
Figure 5A:
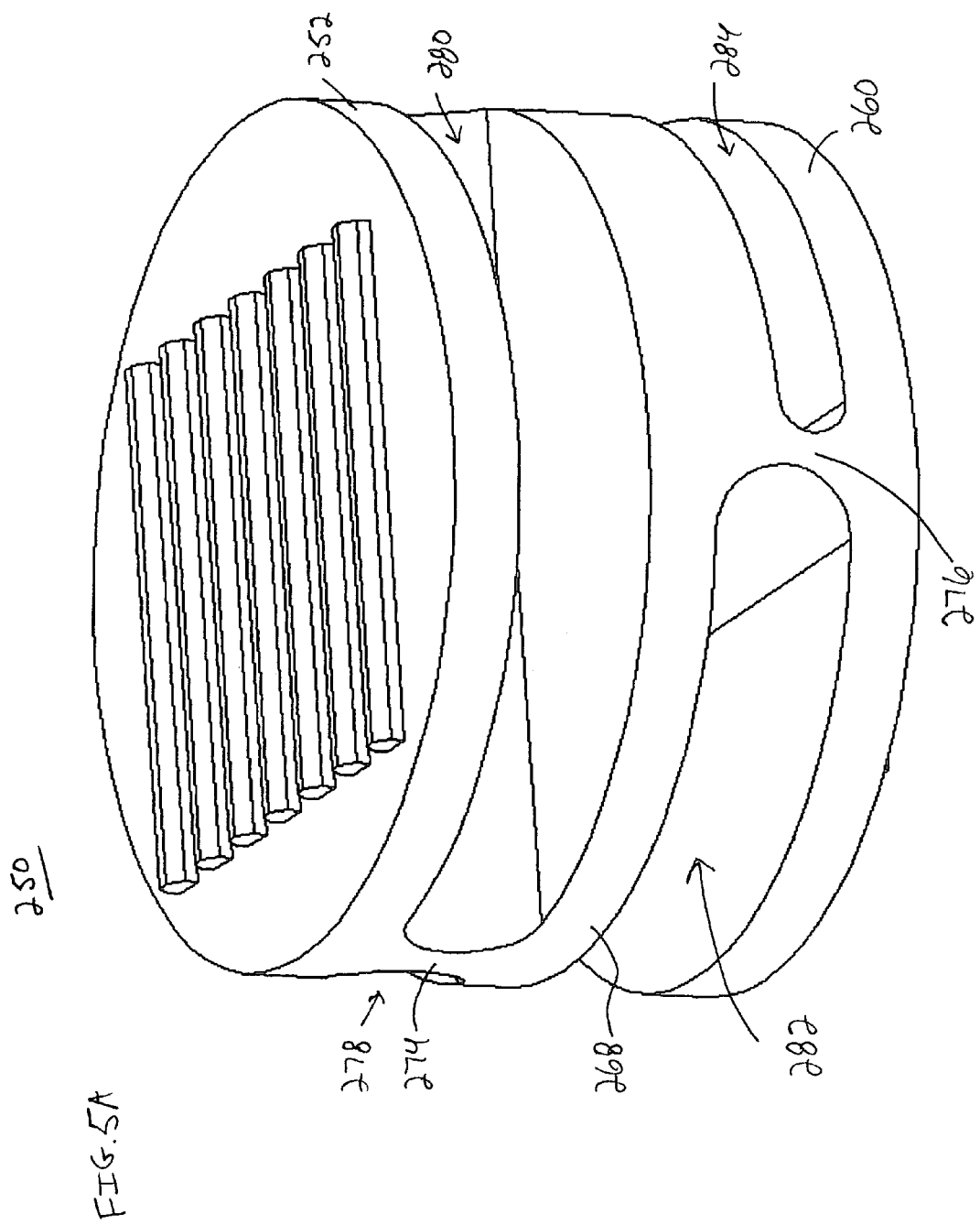
Figure 5C:
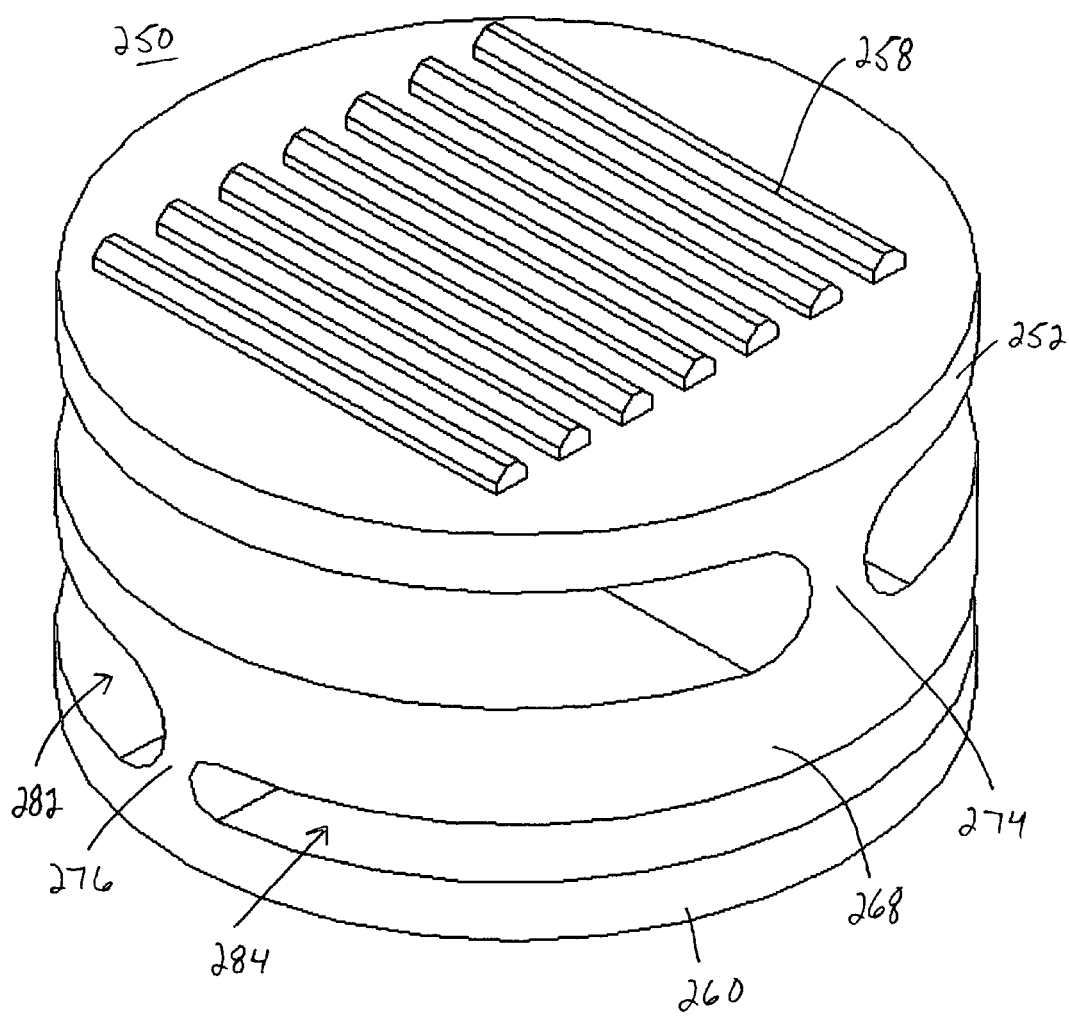
Figure 6A:
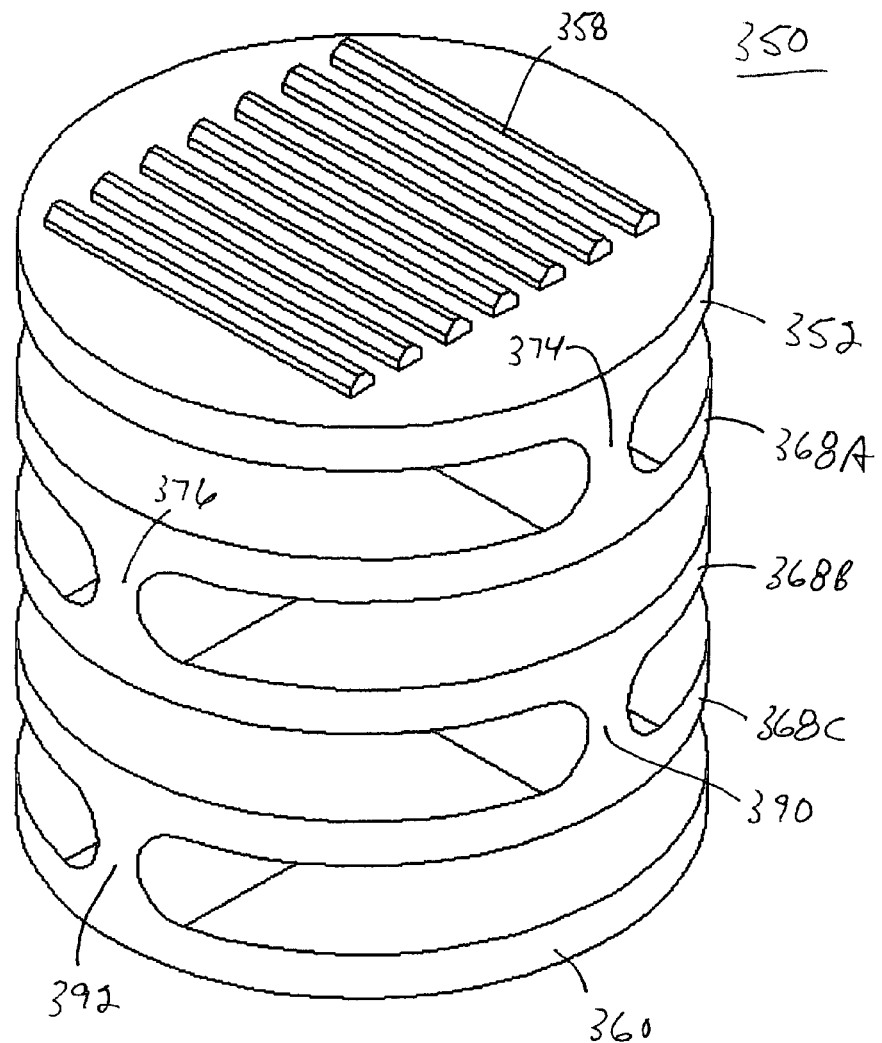

Thus, the embodiment shown in FIGS. 6A-6H has four levels to accommodate a greater spinal gap than could be accommodated by the implant shown above (e.g. the embodiment of FIG. 3A). The exact number of levels may be modified depending upon the size of the spinal segment into which the implant 350 is being inserted. Similar to the structure described above, the implant 350 includes slots formed between opposing plates and on opposite sides of the flexible hinges. The height of one or more of the slots may be different than the heights of the other slots to provide for flexion/extension or lateral bending in one direction that is greater than movement in the opposite direction. One or more of the flexible hinges may have a space formed therethrough, such as shown in the embodiment of FIGS. 4A-4K.

In still other preferred embodiments of the present invention, any of the combination of features found in any of the implants shown herein may be utilized in an implant.

As these and other variations and combinations of the features set forth above can be utilized, the foregoing description of the preferred embodiment should be taken by way of illustration rather than by limitation of the invention.

What is claimed is:

1. An intervertebral implant comprising:
   an upper plate having an outer surface and an inner surface;
   a lower plate having an outer surface and an inner surface;
   a first intermediate plate having a first surface opposing the inner surface of said upper plate and a second surface opposing the inner surface of said lower plate;
   a first flexible hinge formed integrally with said upper plate and said intermediate plate; and
   a second flexible hinge formed integrally with said intermediate plate and said lower plate, wherein the first flexible hinge traverses the second flexible hinge about a vertical axis of the implant;
   wherein the implant is monolithic;
   wherein the implant is not compressible along the vertical axis;
   wherein said implant further comprises first and second slots that extend between said upper plate and said intermediate plate on opposite sides of said first flexible hinge; and
   wherein said first flexible hinge has an opening extending between and in communication with said first slot and said second slot.

2. The implant as claimed in claim 1, wherein said first hinge interconnects said upper plate and said intermediate plate and said second hinge interconnects said intermediate plate and said lower plate.

3. The implant as claimed in claim 1, wherein said implant comprises a flexible material.

4. The implant as claimed in claim 1, wherein said implant comprises a material selected from the group consisting of titanium, thermoplastics, stainless steel and nitinol.

5. The implant as claimed in claim 1, wherein each of said first and second slots has a height that extends between the inner surface of said upper plate and the first surface of said intermediate plate.

6. The implant as claimed in claim 5, wherein the height of one of said first and second slots is greater than the height of the other one of said first and second slots.

7. The implant as claimed in claim 1, wherein said implant further comprises third and fourth slots that extend between said lower plate and said intermediate plate on opposite sides of said second flexible hinge.

8. The implant as claimed in claim 7, wherein each of said third and fourth slots has a height that extends between the inner surface of said lower plate and the second surface of said intermediate plate.

9. The implant as claimed in claim 8, wherein the height of one of said third and fourth slots is greater than the height of the other one of said third and fourth slots.

10. The implant as claimed in claim 7, wherein said second flexible hinge has an opening extending between and in communication with said third slot and said fourth slot.

11. The implant as claimed in claim 7, wherein said first and second slots allow said upper plate and said intermediate plate to angulate relative to one another about a first axis, and said third and fourth slots enable said intermediate plate and said lower plate to angulate relative to one another about a second axis, and wherein said implant is adapted for flexion and extension about one of the first and second axes and lateral bending about the other one of the first and second axes.

12. The implant as claimed in claim 1, further comprising second and third intermediate plates disposed between said first intermediate plate and said lower plate, wherein said first and second intermediate plates are coupled together by a first intermediate hinge and said second and third intermediate plates are coupled together by a second intermediate hinge.

13. The implant as claimed in claim 12, wherein said lower plate is connected to said third intermediate plate by said second flexible hinge.

14. The implant as claimed in claim 1, wherein the outer surface of said upper plate has one or more bone engaging projections and the outer surface of said lower plate has one or more bone engaging projections.

15. The implant as claimed in claim 1, wherein the height of the disc space is preserved.

16. The implant as claimed in claim 1, wherein the vertical axis extends through the upper plate, the first flexible hinge, the first intermediate plate, the second flexible hinge, and the lower plate.

17. The implant as claimed in claim 1, wherein the implant is axially rigid along the vertical axis to support loads on the spine while allowing compliance about the flexible hinges.

18. The implant as claimed in claim 1, wherein when the implant is in a resting state, the vertical axis is substantially perpendicular to the upper plate, the first intermediate plate, and the lower plate.

19. The implant as claimed in claim 1, wherein the first flexible hinge defines a pivot axis that is fixed with respect to portions of the upper and lower plates that coincide with the vertical axis.

20. An intervertebral implant comprising:
an upper plate having an outer surface and an inner surface;
a lower plate coupled with said upper plate, said lower plate having an outer surface and an inner surface;
first, second and third intermediate plates disposed between the inner surfaces of said upper plate and said lower plate;
said first intermediate plate integrally connected with said upper plate by a first flexible hinge, the first intermediate plate having a first surface opposing the inner surface of said upper plate;
said third intermediate plate integrally connected with said lower plate by a second flexible hinge;
said second intermediate plate being disposed between said first and third intermediate plates, said second intermediate plate integrally connected with said first intermediate plate by a first intermediate hinge and integrally connected with said third intermediate plate by a second intermediate hinge, the first intermediate plate having a second surface opposing a surface of said second intermediate plate;
wherein the first flexible hinge traverses the first intermediate hinge, the first intermediate hinge traverses the second intermediate hinge, and the second intermediate hinge traverses the second flexible hinge,
wherein at least one hinge traverses another hinge about a vertical axis of the implant, and the implant is not compressible along the vertical axis;
wherein the implant is monolithic;
wherein said implant further comprises first and second slots that extend between said upper plate and said first intermediate plate on opposite sides of said first flexible hinge; and
wherein said first flexible hinge has an opening extending between and in communication with said first slot and said second slot.

21. The implant as claimed in claim 20, wherein said first flexible hinge and said second intermediate hinge extend along axes that lie in a first plane and said second flexible hinge and said first intermediate hinge extend along axes that lie in a second plane.

22. An intervertebral implant comprising:
an upper plate having an outer surface and an inner surface, the outer surface of the upper plate including one or more bone-engaging projections;
a lower plate having an outer surface and an inner surface, the outer surface including bone-engaging projections;
an intermediate plate having a first surface that faces toward the inner surface of the upper plate and a second surface that faces toward the inner surface of the lower plate;
a first flexible hinge formed integrally with the upper plate and the intermediate plate;
a second flexible hinge formed integrally with the intermediate plate and the lower plate, the first flexible hinge extending along a first axis and the second flexible hinge extending along a second axis that traverses the first axis about a vertical axis of the implant;
the implant having first and second slots that extend between the upper plate and the intermediate plate, on opposite sides of the first flexible hinge, the slots having a height that extends between the inner surface of the upper plate and the first surface of the intermediate plate, the first flexible hinge having an opening extending between and in communication with said first slot and said second slot;
the implant having third and fourth slots formed on opposite sides of the second flexible hinge, wherein the first and second slots allow the upper plate and the intermediate plate to angulate relative to one another about the first axis, and the third and fourth slots enable the intermediate plate and the lower plate to angulate relative to one another about the second axis, and wherein the implant enables flexion and extension about one of the first and second axes and lateral bending about the other of the first and second axes;
wherein the implant is monolithic; and
wherein the implant is not compressible along the vertical axis.

23. An intervertebral implant comprising:
an upper plate having an outer surface and an inner surface;
a lower plate having an outer surface and an inner surface;
a first intermediate plate having a first surface opposing the inner surface of said upper plate and a second surface opposing the inner surface of said lower plate;
a first flexible hinge formed integrally with said upper plate and said intermediate plate; and
a second flexible hinge formed integrally with said intermediate plate and said lower plate, wherein the first flexible hinge traverses the second flexible hinge about a vertical axis of the implant;
wherein the implant is monolithic;
wherein the implant is not compressible along the vertical axis;
wherein said implant further comprises first and second slots that extend between said upper plate and said intermediate plate on opposite sides of said first flexible hinge;
wherein said implant further comprises third and fourth slots that extend between said lower plate and said intermediate plate on opposite sides of said second flexible hinge; and wherein said second flexible hinge has an opening extending between and in communication with said third slot and said fourth slot.

\* \* \* \* \*